United States Patent [19]

Melasniemi et al.

[11] Patent Number: 4,971,906

[45] Date of Patent: Nov. 20, 1990

[54] AMYLASE OF A NEW TYPE

[75] Inventors: Hannes Melasniemi, Vantaa; Matti Korhola, Helsinki, both of Finland

[73] Assignee: Oy Aiko AB, Helsinki, Finland

[21] Appl. No.: 90,197

[22] Filed: Aug. 27, 1987

[30] Foreign Application Priority Data

Aug. 27, 1986 [FI] Finland .................................. 863484

[51] Int. Cl.$^5$ .............................................. C12P 19/16
[52] U.S. Cl. ...................... 435/98; 435/210; 435/842; 435/911
[58] Field of Search .................. 435/98, 96, 210, 911, 435/842

[56] References Cited

U.S. PATENT DOCUMENTS

| | | | |
|---|---|---|---|
| 4,011,139 | 3/1977 | Horwath | 435/18 |
| 4,247,637 | 1/1981 | Tamura | 435/911 |
| 4,335,208 | 6/1982 | Norman | 435/96 |
| 4,400,470 | 8/1983 | Zeikus | 435/842 |
| 4,405,717 | 9/1983 | Urbas | 435/842 |
| 4,536,477 | 8/1985 | Katkocin | 435/842 |
| 4,612,287 | 9/1986 | Coleman et al. | 435/172.3 |
| 4,613,570 | 9/1986 | Zeman | 435/94 |
| 4,628,028 | 12/1986 | Katkocin et al. | 435/95 |
| 4,628,031 | 12/1986 | Zeikus et al. | 435/205 |
| 4,657,865 | 4/1987 | Takasayi | 435/210 |

FOREIGN PATENT DOCUMENTS

| | | |
|---|---|---|
| 85302258 | 7/1985 | European Pat. Off. . |
| 0184019 | 6/1986 | European Pat. Off. . |
| 0188049 | 7/1986 | European Pat. Off. . |
| WO86/01831 | 3/1986 | PCT Int'l Appl. . |

OTHER PUBLICATIONS

Melasniemi, Journal of General Microbiology, vol. 133, No. 4, pp. 883-890 (1987).
Melasniemi, Biochem. J., vol. 246, pp. 193-197 (1987).
Patent Abstracts of Japan, vol. 2, No. 140, p. 3090 C 78, Nov. 18, 1978.
Hyun and Zeikus, May 1985, General Biochemical Characterization of Thermostable Pullulanase and Glucoamylase from Clostridium Thermonydrosulfuricum, Applied and Environmental Microbiology, pp. 1168-1173.

*Primary Examiner*—Peter D. Rosenberg

[57] ABSTRACT

The present invention relates to α-amylase-pullulanase enzyme of a new type produced by *Clostridium thermohydrosulfuricum* bacterium and to a method for the production of the soluble enzyme by culturing *Clostridium thermohydrosulfuricum* strains. The invention further relates to a method for the production of maltose and maltotriose from starch by using the enzyme.

26 Claims, 6 Drawing Sheets

- ACTIVITY OF α-AMYLASE
○ ACTIVITY OF PULLULANASE

● ACTIVITY OF α-AMYLASE
○ ACTIVITY OF PULLULANASE 1) standards: glucose-maltoheptaosidi;
2) amylose + 1X I, 24 h;
3) pullulanase + 1X I, 24 h;
4) corn starch + 1X I, 24 h;
5) corn starch - 1X II, 24 h;
6) corn starch + 10X II, 24 h;
7) corn starch + 10X II, 48 h;
8) standards: glucose-maltoheptaosidi.

I and II are two homogenous fractions obtained in enzyme purification.

AMYLASE OF A NEW TYPE

BACKGROUND OF THE INVENTION

The present invention relates to an amylase of a new type, an α-amylase-pullulanase enzyme active and stable at high temperatures, by means of which it is possible to produce maltose syrup from starch. This soluble enzyme is produced in the culture medium by certain Clostridium thermohydrosulfuricum strains when they are grown on a culture medium which contains dextrin or small-molecular soluble starch.

The glucose units of starch are linked to each other mainly by α-1,4-glucosidic linkages, forming long chains. In addition, starch has α-1,6-glucosidic linkages, there being such a linkage at each branching site of the chains.

α-Amylases cleave 1,4 linkages of starch at random along the chains, whereas β-amylases cleave the same linkages at the non-reducing ends of the chains. Pullulanases, for their part, are debranching enzymes which cleave the 1,6-linkages at the branching sites.

Maltose syrups are prepared by hydrolyzing starch by means of plant β-amylases or by allowing a saccharifying mold α-amylase to hydrolyze further a starch which has been liquefied using bacterial α-amylase. By both procedures a maltose syrup containing approximately 60% maltose is obtained. Maltose yields higher than this are obtained using β-amylase together with pullulanase. Maltose syrups are used mainly in the candy and bakery industries, because of their typical mild sweet taste, low viscosity, low hygroscopicity, and high thermal stability.

It is advantageous for the starch hydrolysis process if the enzyme used is active and stable at high temperatures. β-Amylases, mold α-amylases, and commercially available pullulanases of Klebsiella pneumoniae and Bacillus sp. cannot, however, be used at temperatures above 60° C. Thus, a maltogenic enzyme with higher thermostability would be advantageous in the production of maltose syrup.

If several enzymes are used in the process, it is usually necessary to make compromises with respect to the activity requirements of the enzymes, or alternatively to use the enzymes in succession and to adjust the process in between. In terms of simplicity and economy it would be better if one single enzyme was sufficient for the process. For this reason the ideal enzyme used for the production of maltose syrup should possess liquefying, saccharifying and starch debranching activity.

Hyun and Zeikus (1985; J. Bacteriol. 49, 1168) studied the degradation of starch by Clostridium thermohydrosulfuricum strain E39 (ATCC 33223) isolated from the hot Octopus spring in Yellowstone National Park in the United States. This strain produced cell-bound pullulanase and glucoamylase but not α-amylase. The preparations obtained from strain E39 hydrolyzed starch, producing glucose, without maltose, maltotriose or maltotetraose being observed as intermediate products.

SUMMARY OF THE INVENTION

The enzyme described in the present invention differs from the amylases previously described, since the said enzyme is an amylase of a completely new type, α-amylase-pullulanase, in which two separate enzyme activities, an α-amylase and pullulanase, are present in the same protein molecule. The α-amylase-pullulanase enzyme described in the present invention degrades starch into maltose and maltotriose.

Production of α-amylase-pullulanase according to the invention has been observed with Clostridium thermohydrosulfuricum strains E 101–69 (DSM 3783) and E 100–69 (DSM 567), which were isolated from Austrian beet sugar factories in 1969 (Hollaus & Klaushofer, 1973; Int. Sugar J., 75, 237–241 and 271–275). Strain E 100–69 is a neotype strain of the bacterium Clostridium thermohydrosulfuricum. C. thermohydrosulfuricum strain E 101–69 was deposited on July 3, 1986 with Deutsche Sammlung von Mikroorganismen in accordance with the conditions of the Budapest Treaty under the above-mentioned deposit number DSM 3783. Strain E 100–69 was deposited with the same collection previously by its discoverers.

Several strains of the yeast Saccharomyces cerevisiae are capable of using maltose and maltotriose as their sources of carbon, to produce ethanol (Steward & Russel, 1983; in Yeast Genetics, Fundamental and Applied Aspects, p. 461, eds. J. Spencer, D. Spencer and A. Smith, Springer-Verlag, New York). Since α-amylase-pullulanase degrades starch specifically into a mixture of these sugars, ethanol can be produced from starch by yeast by using α-amylase-pullulanase as the mashing enzyme.

BRIEF DESCRIPTION OF THE DRAWINGS

The accompanying figures relating to the examples depict the properties of the α-amylase-pullulanase according to the invention, as follows.

DETAILED DESCRIPTION OF THE INVENTION

Determination of the Enzyme Activities

The α-amylase and pullulanase activities were determined by measuring the rate of reducing sugars released by them from pure amylose (type III: from potato, Sigma Chemical Co. Ltd., St. Louis, MO 63178, USA) and from pullulan (Sigma). 25 μl of enzyme was added to one milliliter of 0.5% substrate in a 100 mM sodium acetate buffer adjusted to pH 5.6, containing 2 mM $CaCl_2$, 0.1 mM $Na_2$-EDTA and 50 mM NaCl. The reducing sugars were determined by the Nelson-Somogyi method (Nelson, 1944; J. Biol. Chem., 153, 375; Somogyi, 1952; J. Biol. Chem., 195, 19) after the tubes had been incubated for 15 min at 85° C. In the above mentioned assay, the reducing sugar released by one α-amylase or pullulanase enzyme unit, corresponds to one nanomole of anhydrous glucose. The amylose was brought into solution by 1M NaOH, which was neutralized with HCl, the buffer was added, and finally the solution was filtrated using a 1.2 μm RAWP membrane filter (Millipore Corp., Ashby Road, Bedford, MA 01730, USA).

The protein was determined by the method of Lowry (Lowry et al., 1952; J. Biol. Chem., 193, 256) with ovalbumin (fraction V, Sigma) as the standard.

| Composition of the medium used | |
|---|---|
| Constituent: | g, $l^{-1}$ |
| Soluble starch (according to Zulkowsky), | 20.0 |
| (E. Merck, Darmstadt, Federal Republic of Germany) | |
| Yeast extract | 5.0 |
| (Difco Laboratories, Detroit, Michigan, USA) | |
| Tryptone | 10.0 |
| (Difco) | |
| Meat extract (Lab-Lemco), | 5.0 |
| (Oxoid Ltd., Basingstoke, Hampshire, England) | |
| $KH_2PO_4$ | 6.8 |
| $K_2HPO_4.3H_2O$ | 11.4 |
| $FeSO_4.7H_2O$ | 0.02 |
| $MgSO_4.7H_2O$ | 0.01 |
| $CaCl_2.2H_2O$ | 0.01 |
| pH 6.8 | |

Characterization of the Raw Enzyme

Strain E 101-69 was cultured in a two-liter flask, without stirring, for 30 h under anaerobic conditions at 68° C. on the medium described above, to which resazurine 1 mg $l^{-1}$ and thioglycolic acid 200 $\mu l$ $l^{-1}$ had been added. The cells were removed by centrifugation, whereafter the raw preparation of α-amylase-pullulanase was precipitated out from the culture medium supernatant, the α= amylase activity of which was 520 U $ml^{-1}$ and pullulanase activity 1550 U $ml^{-1}$, by making it 70% saturated with respect to ammonium sulfate. Some of the essential properties of the enzyme were characterized by using this raw preparation having an α-amylase activity of 12000 U $ml^{-1}$ and a pullulanase activity of 37000 U $ml^{-1}$.

Figure 1:
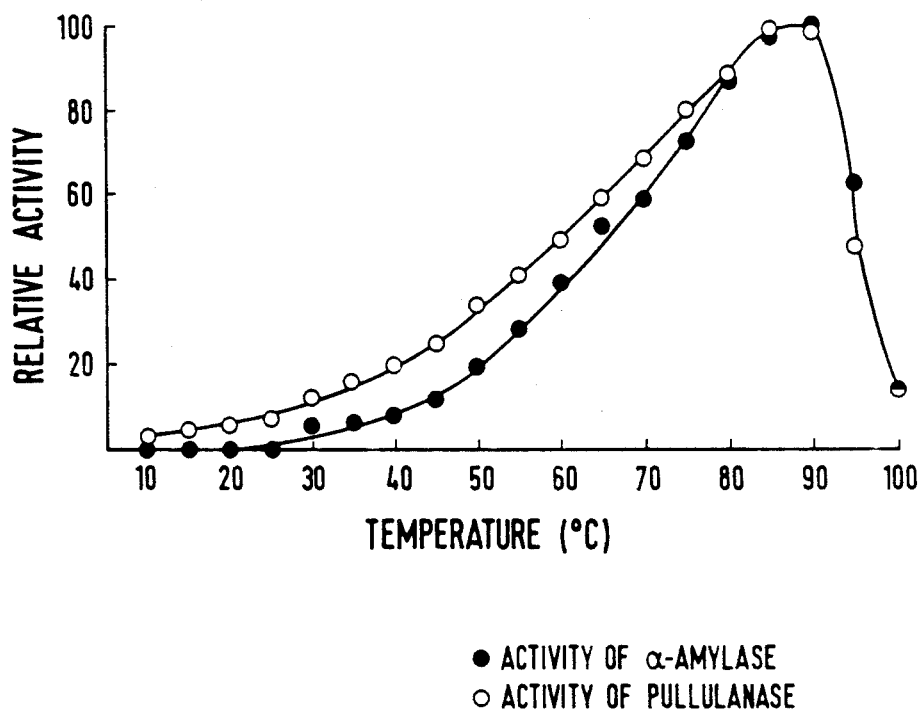
FIG. 1. Effect of temperature on the activity of α-amylase-pullulanase.

Both activities of the enzyme had their temperature optimum at 85° C. (FIG. 1) when the α-amylase and pullulanase activities of diluted raw enzyme (1200 U $ml^{-1}$ α-amylase and 3700 U $ml^{-1}$ pullulanase) were determined by the procedure described above but by using different temperatures.

Figure 2A:
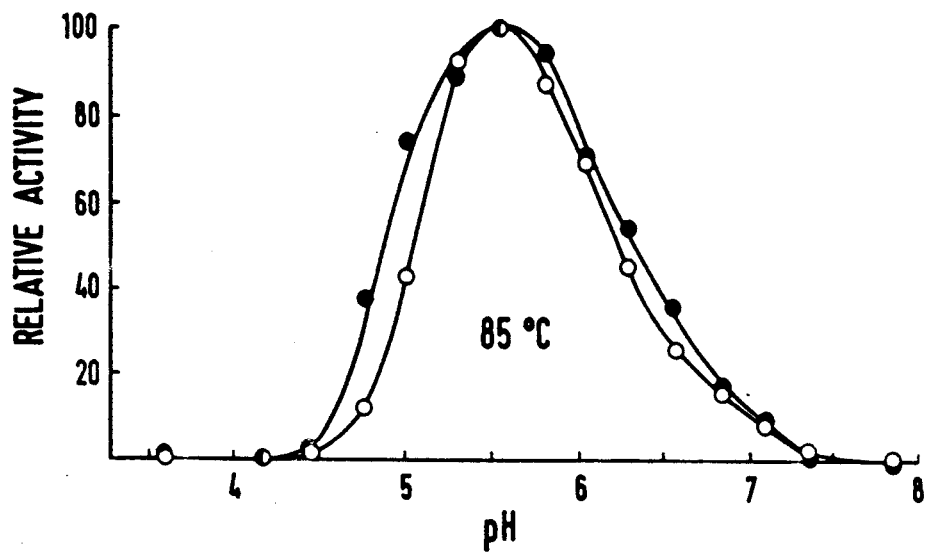
FIG. 2. Effect of pH on the activity of α-amylase-pullulanase, at 85° C. (A) and 60° C. (B).
Figure 2B:
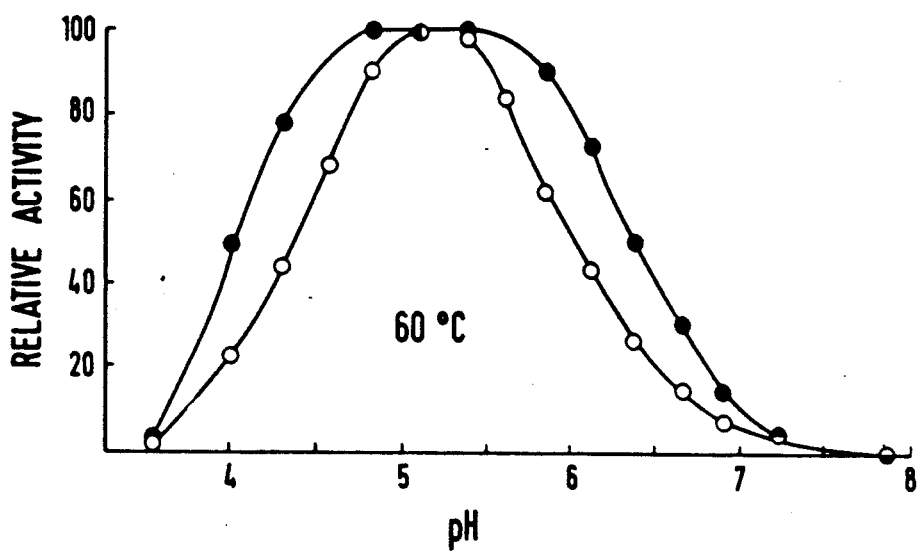
Figure 3:
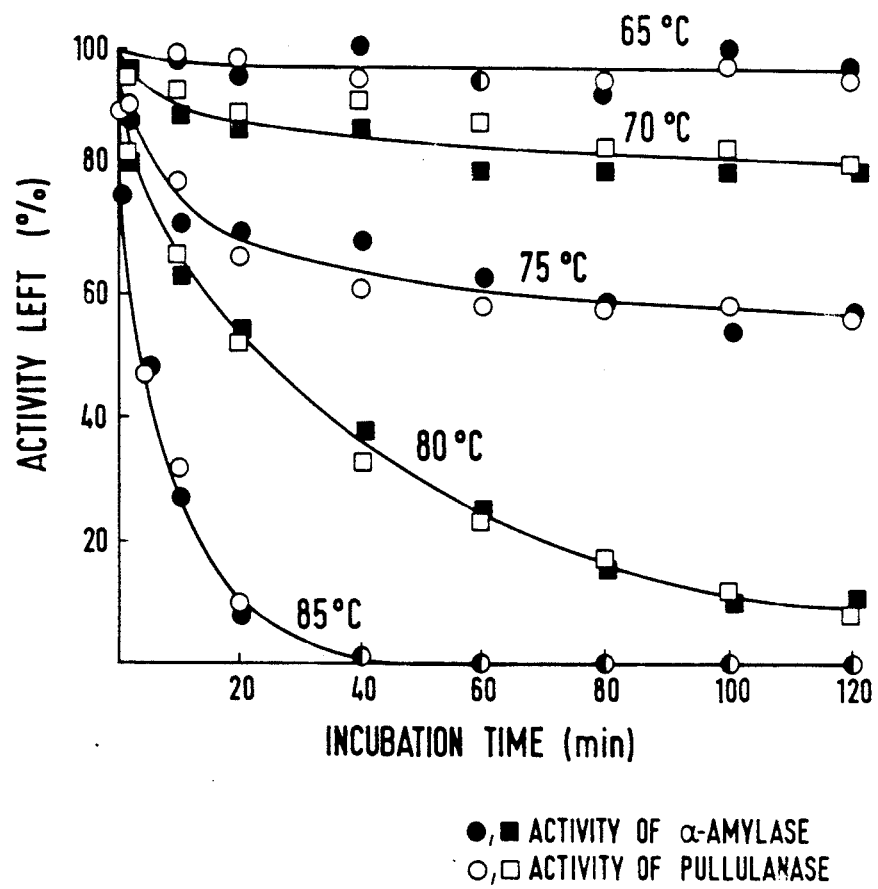
FIG. 3. Inactivation of α-amylase-pullulanase at different temperatures in a buffer, without substrate and calcium.

The pH optimum of both activities was 5.6 when the determinations were made at 85° C. (FIG. 2A) and 5.2 when the determinations were made at 60° C. (FIG. 2B); a value of 100 has been given in the figure for the highest activities at both temperatures. 25 $\mu l$ of diluted raw enzyme (30 U of α-amylase and 90 U of pullulanase) was added to 1 ml of a 100 mM sodium citrate buffer adjusted to different pH values and containing 0.5% amylose or pullulan, 50 mM NaCl and 10 mM $CaCl_2$. The tubes were thereafter incubated for 15 min at 85° C. or 60° C., and the reducing sugars released were determined.

Both of the activities were stable at 60° C., but they became inactivated in the same manner at higher temperatures when they were incubated in a 100 mM sodium acetate buffer, pH 5.6, at different temperatures, the final concentration of α-amylase being 800 U $ml^{-1}$ and of pullulanase 2400 U $ml^{-1}$. The remaining α-amylase and pullulanase activities were determined by the procedure described above by using 50 $\mu l$ samples which were taken at the times shown in the figure.

Figure 4:
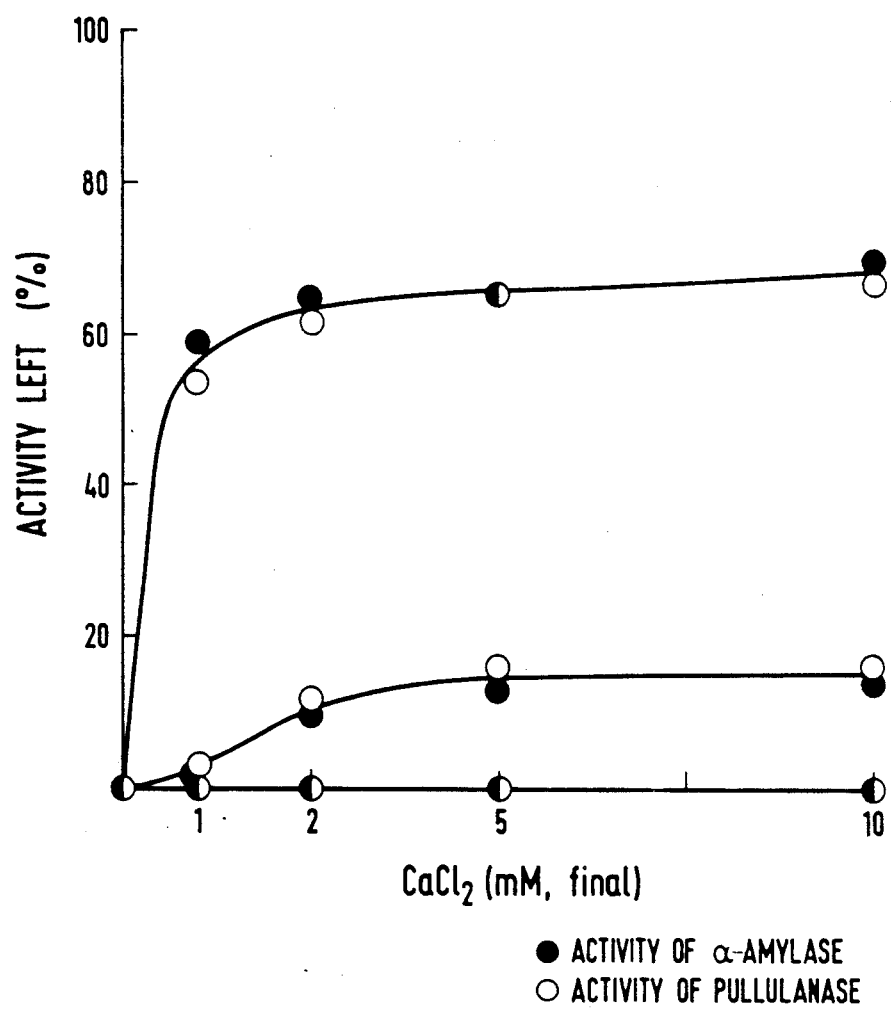
FIG. 4. Stabilization of α-amylase-pullulanase by calcium at high temperatures.

Calcium ions stabilized both the activities in the same manner at high temperatures (FIG. 4). Raw enzyme was added to give a final concentration of 800 U $ml^{-1}$ of α-amylase and 2400 U $ml^{-1}$ of pullulanase in a 100 mM sodium acetate buffer, pH 5.6, containing different amounts of calcium. This was incubated for 2 h at temperatures of 85° C., 90° C. and 95° C. The remaining α-amylase and pullulanase activities were determined by the procedure described above using 50 $\mu l$ samples.

Purification of the Enzyme

The soluble α-amylase-pullulanase enzyme was purified from the culture broth of strain E 101-69 as follows. The strain was cultured anaerobically for 40 h at 68° C. in a 22-liter flask, without stirring, in the medium described above. After the cells had been removed by centrifugation, wheat starch (BDH Chemicals Ltd., Broom Road, Poole BH12 4NN, England) 15 g $l^{-1}$ and sodium azide 200 mg $l^{-1}$ were added to the cold supernatant, and it was then stirred in the cold for 90 h in order to absorb the enzyme to the starch. Thereafter the starch was allowed to settle for 24 h, the supernatant was removed, and the starch cake which had settled on the bottom was washed by slurrying it into two liters of ice-cold water and by centrifugation. The adsorbed enzyme was detached from the starch by extracting it in a hot bath, by mixing it with two, half liter batches of 60° C. water and by centrifugation.

The extracts were made 20 mM by using strong sodium acetate adjusted to pH 5.6 and were applied to a 2.6×15 cm DEAE cellulose column (DE 52; Whatman Ltd, Springfield Mill. Maidstone, Kent, England) equilibrated using the same buffer. The column was washed with the equilibrated buffer and eluted then first with 100 mM and thereafter with 200 mM sodium chloride in the same buffer. The eluates obtained using the stronger salt were combined and concentrated to 21 ml by using an ultrafiltration chamber (Amicon Corp., Danvers, Massachusetts, USA) equipped with a PM 10 membrane.

The sample was dialyzed against a 10 mM potassium phosphate buffer, pH 7.0, and was applied to a 2.6×13 cm hydroxyapatite column (Bio Gel HT, Bio Rad, 1414 Harbour Way South, Richmond, Calif. 94804, USA) equilibrated using the same buffer. The column was first washed with the equilibration buffer and then eluted using a 10–400 mM potassium phosphate gradient, pH 7.0. The enzyme was eluted as a peak which was followed by a shoulder having a clearly lower specific activity. The fractions eluted in the peak were combined and concentrated, as above, to a volume of 1 ml.

The concentrated sample was run in 200 $\mu l$ batches through combined Superose ™ 12 and 6 gel filtration columns (Pharmacia Fine Chemicals, Uppsala, Sweden) in a 50 mM ammonium acetate buffer, pH 6.5, at a rate of 6 ml $h^{-1}$. The enzyme eluted as two adjacent peaks, and the material (I and II) contained in them was lyophilized. The specific α-amylase activity of preparation I at this stage was 39 kU $mg^{-1}$ and its specific pullulanase activity 101 kU $mg^{-1}$, the respective specific activities of preparation II being 36 kU $mg^{-1}$ and 90 kU $mg^{-1}$.

Both preparations were thereafter gel filtered using a Superose ™ 6 column in denaturing conditions in the presence of 6M guanidine hydrochloride and β-mercaptoethanol. It has been observed that in these conditions proteins in general lose all of their non-covalent structure and dissociate into their subunits (Tanford, 1968, Advan. Protein Chem., 23, 121). Before the gel filtration the samples were dissolved in a sample buffer having the following composition: 7.3M guanidine hydrochloride, 0.1M sodium acetate, 0.02M EDTA, 0.5M β-mercaptoethanol, and a pH of 8.1. The samples were incubated at 50° C. for 4 h, the pH was adjusted to 5.0, and the samples were then run in 200 μl batches at a flow rate of 1 ml h$^{-1}$, the buffer consisting of 6M guanidine hydrochloride, 100 mM sodium acetate, 20 mM β-mercaptoethanol, and having a pH of 5.0. The fractions in which the enzyme eluted were combined and dialyzed thoroughly against a 20 mM ammonium hydrogen carbonate buffer, pH 7.9. The renatured enzyme preparations (I and II) thus obtained, which were homogenous according to both SDS-polyacrylamide gradient gel electrophoresis (cf. leaflet, "Calibration kits for molecular weight determination using electrophoresis"; Pharmacia Fine Chemicals, Uppsala, Sweden, 1982) and gel filtration performed in guanidine hydrochloride, were used for further characterization of the enzyme.

Carbohydrate Bound to the Enzyme

The purified α-amylase-pullulanase contained carbohydrate. Upon hydrolysis the enzyme released sugars having the same mobility as mannose, glucose, galactose and ramnose on thin layer chromatography on a Silica gel 60 plate (No. 5553, E. Merck) saturated with 0.2M NaH$_2$PO$_4$, with a mixture of n-butanol, acetone and water (4:5:1, v/v) as the eluent. The amount of neutral hexoses was estimated as 10% of the total amount of protein and neutral hexoses when the neutral hexoses were determined by the Antron method (Spiro, 1965; Methods in Entzymology, vol. 8, p. 3) with mannose as the standard.

Molecular Weight of the Enzyme

SDS-polyacrylamide gradient gel electrophoresis with PAA 4/30 gels (Pharmacia Fine Chemicals) showed that the α-amylase-pullulase consisted of subunits of only one type, having an exceptionally high molecular weight. The relative molecular weight obtained for the enzyme subunit was 190000±30000 by using preparation I and 180000±30000 by using preparation II. In native operating conditions, with the same gels, the relative molecular weight obtained for the renatured α-amylase-pullulanase was 370000±85000 by using preparation I and 330000±85000 by using preparation II. The bands obtained from the enzyme by gradient gel electrophoresis were very diffuse. On the other hand, by guanidine hydrochloride gel filtration a sharp, symmetric peak was obtained at a point corresponding to a relative molecular weight of 275000±50000. This method did not distinguish preparations I and II from one another in a sample which contained both.

Hydrolysis of Starch at Different Temperatures

Figure 5:
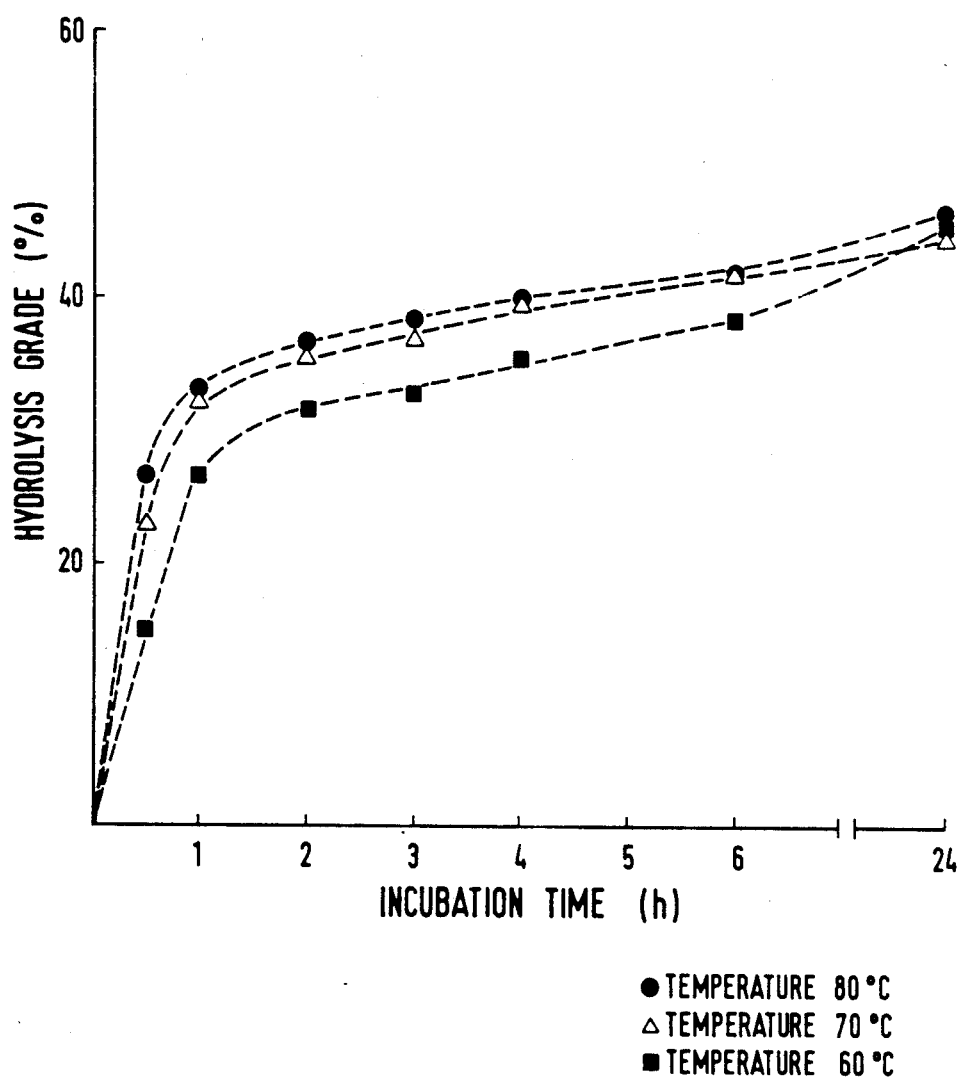
FIG. 5. Hydrolysis of starch by purified α-amylase-pullulanase, at different temperatures.

The presence of substrate, stabilized α-amylase-pullulanase so that it was possible to use the enzyme for the hydrolysis of starch at 80° C. as well as at 60° C. (FIG. 5). Purified α-amylase-pullulanase was added at 480 U ml$^{-1}$ α-amylase and 1100 U ml$^{-1}$ pullulanase into tubes which contained in a 100 mM sodium acetate buffer; 0.5% corn starch (Sigma), 2 mM CaCl$_2$, 0.1 mM Na$_2$-EDTA, 50 mM NaCl, and had a pH of 5.6. The tubes were incubated at temperatures of 60° C., 70° C. and 80° C., and their reducing sugars were determined from samples taken at the times shown in the figure. The hydrolysis percentage was calculated by comparing the amount of reducing sugars present in the samples to the amount of reducing sugars present in the substrate hydrolyzed into glucose by using dilute acid (0.5N HCl, 100° C., 3 h).

End Products Formed by the Enzyme

The end products formed by α-amylase-pullulanase were determined as follows. 0.5% solutions were prepared from amylose (type III: from potato), pullulan, and corn starch (all from Sigma) in a buffer (100 mM sodium acetate, 2 mM CaCl$_2$, 0.1 mM Na$_2$-EDTA, 50 mM NaCl, pH 5.6), purified α-amylase pullulanase preparation I or II was added to the solutions, and they were incubated at 80° C. The enzyme was used in two concentrations, 480 U ml$^{-1}$ α-amylase and 1100 U ml$^{-1}$ pullulanase (=1X) and ten times stronger (=10X). Samples taken from the hydrolysates after 24 h and 48 h were pipetted onto Silica gel 60 plates (No. 5553, E. Merck) and eluted with a mixture of 2-propanol, acetone and water (2:2:1, v/v).

Figure 6:
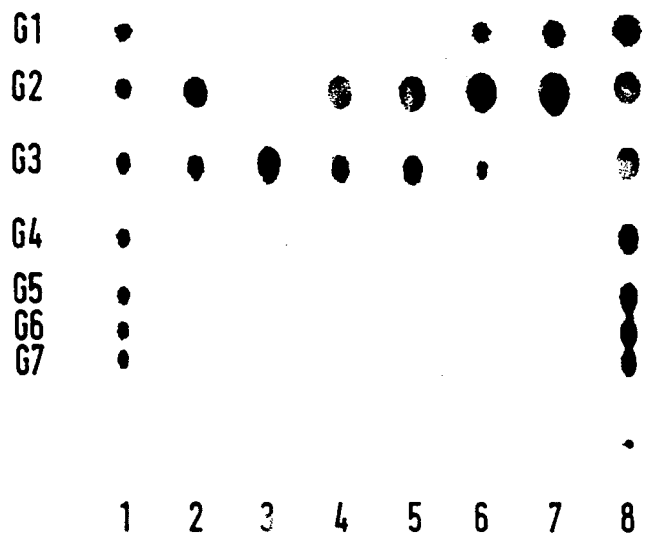
FIG. 6. A thin layer chromatogram of the final products formed by α-amylase-pullulanase.

Purified α-amylase-pullulanase (1X) degraded the pullulan into maltotriose, whereas both the potato amylose and the corn starch were degraded into maltose and maltotriose (FIG. 6). When the higher enzyme concentration (10X) was used, it was observed that the maltotriose was degraded further (FIG. 6). In this case, 77% maltose, 15% glucose and 4% maltotriose were produced from corn starch in a 48 h hydrolysis. The maltose and the maltotriose were quantified by liquid chromatography in a column packed with Nucleosil 5 C$_{18}$ reversed-phase material (Macherey-Nagel, D-5160 Düren, Federal Republic of Germany) with water as the eluent, and the glucose was quantified enzymatically (UV test kit No. 716 251, Boehringer-Mannheim, Mannheim, Federal Republic of Germany). The percentages of the hydrolysis products were calculated by comparing their amounts to the amount of substrate hydrolyzed into glucose by using dilute acid (0.5 N HCl, 100° C., 3 h).

Comparision of Strains E 101-69 and E 100-69

Strains E 101-69 and E 100-69 were cultured anaerobically, without shaking, at 68° C. for 24 h on the medium described above, to which resazurin 1 mg l$^{-1}$ and thioglycolic acid 200 μl$^{-1}$ had been added. The cells were removed by centrifugation, and from the supernatants were partly purified α-amylase pullulase preparations, having a specific α-amylase activity of 21 kU mg$^{-1}$ and a specific pullulanase activity of 63 kU mg$^{-1}$ with strain E 101-69 and respective specific activities of 20 kU mg$^{-1}$ and 56 kU mg$^{-1}$ with strain E 100-69. After running SDS-polyacrylic amide gels of these preparations, both showed only a few clearly weaker bands in addition to a strong diffuse band moving with the same mobility as the α-amylase-pullulanase of strain E 101-69 which had previously been purified to a homogenous state.

We claim:

1. An isolated enzyme comprising a protein molecule having both alpha-amylase activity and pullulanase activity wherein said enzyme degrades starch into maltose and maltotriose and said enzyme or the DNA sequence coding for it is derived from a strain of the genus Clostridium.

2. The enzyme of claim 1 wherein its relative molecular weight, as determined by polyacrylamide gradient gel electrophoresis, is 185000±40000 in the presence of sodium dodecyl sulfate.

3. The enzyme of claim 1 wherein the optimum temperature of both enzyme activities is about 80° to 90° C.

4. The enzyme of claim 3 wherein the optimum temperature of both enzyme activities is about 85° C.

5. The enzyme of claim 4 wherein at 85° C. the optimum pH is about 5 to 6.

6. The enzyme of claim 5 wherein at 85° C. the optimum pH is about 5.6.

7. The enzyme of claim 1 wherein at 60° C., the optimum pH is about 4.5–5.5.

8. The enzyme of claim 7 wherein at 60° C., the optimum pH is about 5.2.

9. The enzyme of claim 2 wherein the optimum temperature of both enzyme activities is about 80° to 90 ° C.

10. The enzyme of claim 9 wherein the optimum temperature of both enzyme activities is about 85° C.

11. The enzyme of claim 10 wherein at 60° C. the optimum pH is about 5 to 6.

12. The enzyme of claim 11 wherein at 60° C. the optimum pH is about 5.6.

13. The enzyme of claim 2 wherein at 60° C., the optimum pH is about 4.5 to 5.5.

14. The enzyme of claim 13 wherein at 60° C., the optimum pH is about 5.2.

15. The enzyme of claim 1 wherein said enzyme is produced by using *Clostridium thermohydrosulfuricum* strains.

16. The enzyme of claim 2 wherein said enzyme is produced by using *Clostridium thermohydrosulfuricum* strains.

17. The enzyme of claim 3 wherein said enzyme is produced by using *Clostridium thermohydrosulfuricum* strains.

18. A method of producing an enzyme having both alpha-amylase activity and pullalanase activity which comprises:

culturing a *Clostridium thermohydrosulfuricum* strain on a substrate containing starch or a starch hydrolysate at a temperature of about 42° to 78° C. and at a pH of about 6 to 8; and recovering the enzyme having both alpha-amylase activity and pullalanase activity formed.

19. The method of claim 18, wherein said temperature is about 55° to 75° C. and said pH is about 7.

20. A method for producing maltose and maltotriose from starch or a starch hydrolysate which comprises:

reacting an enzyme comprising a protein molecule having both alpha-amylase activity and pullulanase activity, wherein said enzyme or the DNA sequence coding for it is derived from a strain of the genus Clostridium, with said starch or said starch hydrolysate at a temperature above 60° C. and at a pH of about 4 to 6.5.

21. An isolated enzyme characterized by the following properties:

it has both α-amylase avtivity and pullulanase activity, under the effect of which starch is degraded into maltose and maltotriose;

the enzyme or the DNA sequence coding for it is derived from a strain of the genus Clostridium;

the optimum temperature of both activities is about 80° to 90° C.; and the optimum pH at 85° C. is about 5 to 6.

22. The enzymes of claim 1, which is homogeneous according to both SDS-polyacrylamide gradient gel electrophoresis and gel filtration as defined in the specification.

23. The enzyme of claim 21, which is isolated from *Clostridium thermohydrosulfuricum* strain E 101–69 (DSM 3783) or E 100–69 (DSM 567).

24. A substantially homogeneous enzyme characterized by the following properties:

it has both alpha-amylase activity and pullulanase activity, under the effect of which starch is degraded into maltose and maltotriose;

the enzyme or the DNA sequence coding for it is derived from a strain of the genus Clostridium;

its relative molecular weight, as determined by polyacrylamdie gradient gel electrophoresis, is 185000±40000 in the presence of sodium dodecyl sulfate;

the optimum temperature of both enzyme activities is about 80° to 90° C.; and the optimum pH at 85° C. is 5 to 6 and the optimum pH at 60° C. is 4.5–5.5.

25. The enzyme of claim 1, which has a relative degree of pullulanase activity and alpha-amylase activity of from about 3:1 to about 2.3:1.

26. The enzyme of claim 24, which has a relative degree of pullulanase activity and alpha-amylase activity of from about 3:1 to about 2.3:1.

* * * * *

UNITED STATES PATENT AND TRADEMARK OFFICE
CERTIFICATE OF CORRECTION

PATENT NO. : 4,971,906

DATED : Nov. 20, 1990

INVENTOR(S) : Melasniemi et al

It is certified that error appears in the above-identified patent and that said Letters Patent is hereby corrected as shown below:

On the title page:

In the category "[73] Assignee:" change Aiko" to --Alko--.

Signed and Sealed this

Ninth Day of March, 1993

Attest:

STEPHEN G. KUNIN

*Attesting Officer*     *Acting Commissioner of Patents and Trademarks*